March 15, 1927.
Re. 16,570
M. V. BAUER
SANITARY PAD
Original Filed Oct. 31, 1919
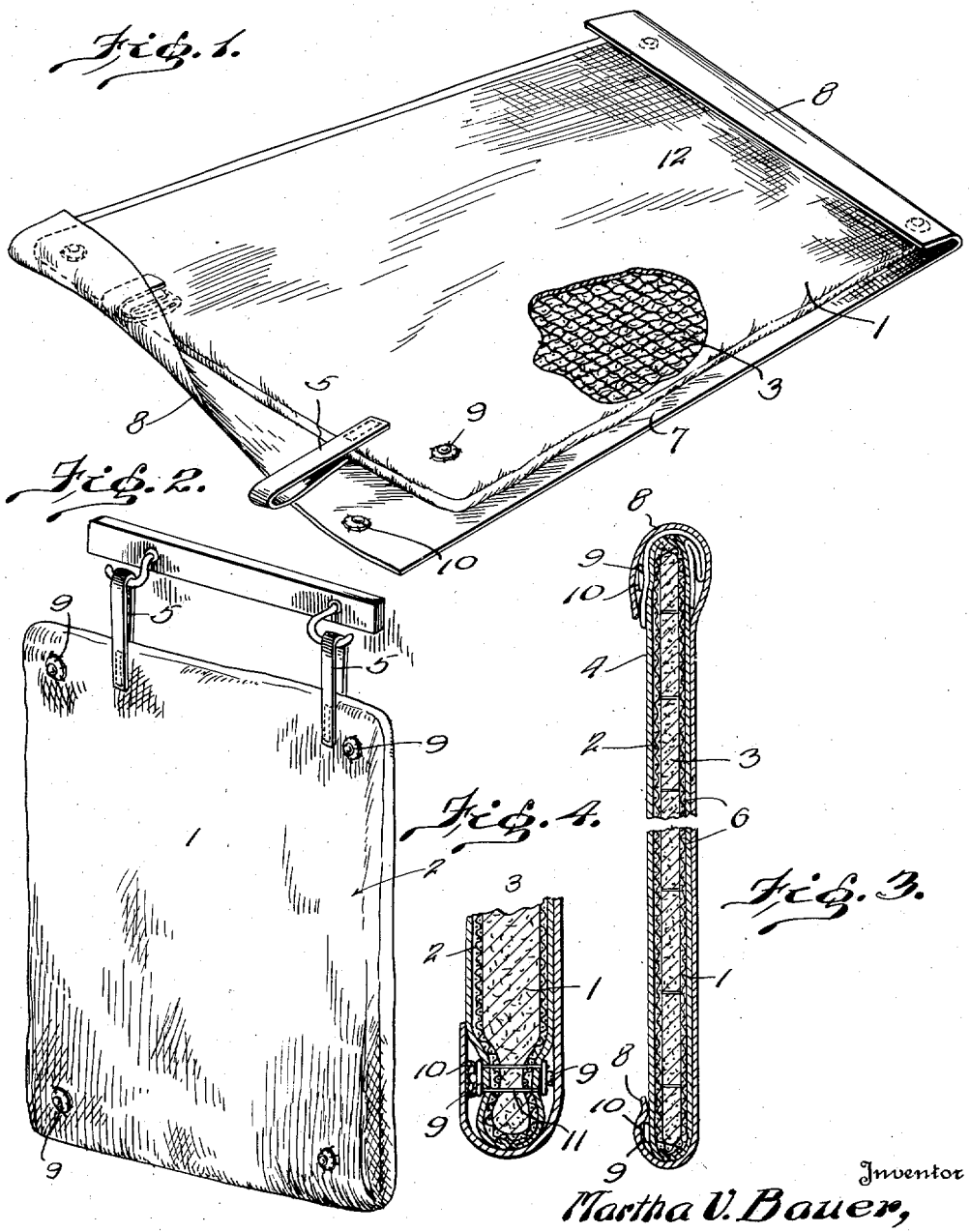
Inventor
Martha V. Bauer,
By Semmes & Semmes
Attorneys Reissued Mar. 15, 1927. Re. 16,570

UNITED STATES PATENT OFFICE.

MARTHA V. BAUER, OF WASHINGTON, DISTRICT OF COLUMBIA.

SANITARY PAD.

Original No. 1,341,875, dated June 1, 1920, Serial No. 334,784, filed October 31, 1919. Application for reissue filed May 29, 1922. Serial No. 564,628.

This invention relates to pads which may be used in any case where absorbent pads are required, and has as one of its primary objects to provide an absorbent pad which may be washed without injury to the filling therein.

Another object of the present invention is to provide an absorbent pad which is filled with sponge and so constructed that the sponge filling therein cannot become displaced while the pad is in use nor during the process of washing the same.

A further object of the present invention is to provide a sanitary pad comprising a washable absorbent member and a detachable non-absorbent backing member.

Another object of the present invention is to provide an absorbent pad comprising a filling of absorbent material, an open mesh inner covering, means to prevent bunching of the filling within said covering, and a soft finely woven outer covering having a smooth unquilted surface.

In the accompanying drawings:

Figure 1 is a perspective view of the pad embodying the present invention:

Fig. 2 is a perspective view of the pad in suspended position;

Fig. 3 is a longitudinal sectional view through the pad;

Fig. 4 is a detail sectional view similar to Fig. 3.

Corresponding and like parts are referred to in the following description and indicated in all the views of the accompanying drawings by the same reference characters.

The absorbent member of the pad is indicated in the drawings in general by the numeral 1 and the same comprises an inner covering or sack 2 which may be of muslin, cheesecloth, netting, or any similar cloth material which is foraminous to a marked degree. This inner covering or sack may be rectangular or any other desired contour and the same is provided with a filling 3 comprising one or more layers of sponge or any other highly absorbent and yieldable material. This member of the pad is generally of a flat form and by reason of the nature of the materials of which it is composed, it will prove soft and comfortable to the person using the article. The absorbent member is completed by an outer covering 4 which may be of muslin or any other soft cloth material which is preferably less foraminous than the inner covering or sack 2 so as not to prove irritating to a person using the pad. It will be understood that both the inner covering or sack 2 and outer covering 4 may be made up in any desired manner each either from one piece or several pieces the edges of which may be united by stitching or otherwise.

In order to adapt the absorbent member of the pad to be suspended as shown in Fig. 2 of the drawings and thus facilitate drying of the same, the said member is provided preferably at one end with suspension loops indicated by the numeral 5, which loops may be formed from suitable lengths of tape in the manner clearly shown in Fig. 1 of the drawings, the ends of the length of tape being stitched or otherwise secured to the said end of the absorbent member. In any event, these loops are of a material which is flexible so that the loops may be folded under conditions to be presently explained.

In order to prevent bunching or shifting of the sponge or other absorbent filling 3 and to maintain the flat contour of the absorbent member as a whole, it is preferable that the member be quilted or tufted, as for example by stitches 6 run through the opposite sides of the inner covering or sack 2 and through the filling 3 at suitably spaced intervals. In this manner the filling will be prevented from bunching or shifting while the pad is in use, and likewise this result will be obtained while the absorbent member is being washed or otherwise cleansed.

In order to prevent any fluids absorbed by the member heretofore described, coming in contact with adjacent materials and soiling the same, a backing sheet is provided for the absorbent member and this sheet is indicated in general by the numeral 7 and is preferably of rubberized cloth or any other flexible sheet material which is non-absorbent. This backing sheet is of the same general marginal contour as the absorbent member but of slightly greater dimensions so that at least two marginal portions thereof, for example the two end marginal portions, indicated by the numeral 8, may be folded over the corresponding ends of the absorbent member when the absorbent member is laid flat upon the spread out backing sheet 7. In order to provide for holding the backing sheet assembled with the absorbent member, the latter is provided at each of its four corners, on both sides or faces of the pad, with one element 9 of a snap fastening, and the backing sheet 7 is provided at each of its four corners with the other element 10 of such a fastening. For example, the absorbent member will be provided with the stud elements of snap fasteners and the backing sheet will be provided with the socket elements of such fasteners, but if desired other types of fastening devices such for example as hooks and eyes may be employed. It will be observed by reference to Fig. 1 of the drawings that when the absorbent member is laid out upon the backing sheet 7, the suspension loops 5 will project beyond the end of the absorbent member and over the face of the backing sheet at the corresponding marginal portion 8 thereof, and in folding over the said marginal portion of the backing sheet as shown in the said figure, it will be desirable to likewise fold over the said suspension loops so that the same will be covered and protected against being torn loose, and likewise prevented from coming in contact with the person using the pad and causing irritation or annoyance.

While but a single one of the elements 9 need be provided at each corner of the absorbent pad member in order to produce a complete structure, nevertheless it will no doubt be desirable to provide two of these elements at each corner, each located upon a respective side or face of the absorbent member and both secured in place by the same stitches, as clearly shown in Fig. 4 of the drawings, these stitches being indicated by the numeral 11 and passing through the inner covering or sack 2, the filling 3, and the outer covering 4. By providing these elements upon both sides or faces of the absorbent member, I am enabled to reverse said member. It will also be evident that the stitches 11 serve as an additional means to prevent displacement or bunching of the filling 3 in the inner covering.

If desired the backing sheet 7 instead of being folded over the opposite ends of the absorbent member, may be made of such size that the ends of said backing sheet, when positioned on said member, will terminate substantially flush with the ends of the absorbent member so that the upper face of said member will present a smooth continuous surface.

While I have thus disclosed the nature of my invention, although without attempting to set forth the various modifications which may be made in carrying out or embodying the same, nor the various purposes for which it may be employed, I wish it to be understood that my invention shall only be limited by the scope of the appended claims and the showing of the prior art.

What I claim as new and desire to secure by Letters Patent, is—

1. An absorbent body comprising an inner covering of foraminous material, a filling of absorbent material therein, means passing through said inner covering and filling to restrain bunching of said filling, and an outer covering of foraminous material over said inner covering and filling.

2. An absorbent body comprising an inner covering of relatively highly foraminous material, a filling of absorbent material therein, means passing through said inner covering and filling to restrain bunching of said filling, and an outer covering of less foraminous material over said inner covering and filling.

3. In an article of manufacture, an absorbent member comprising an inner covering of foraminous material, a filling of absorbent material therein, means passing through said inner covering and filling to restrain bunching of said filling, and an outer covering of foraminous material inclosing said inner covering and filling, a non-absorbent backing sheet and means whereby the absorbent member and backing sheet may be detachably held together.

4. In an article of manufacture, an absorbent pad comprising an inner covering of foraminous material, a filling of absorbent material therein, means passing through said inner covering and filling to prevent bunching of said filling, and an outer covering of foraminous material inclosing said inner covering and filling, a non-absorbent backing sheet having marginal portions extending over corresponding marginal portions of the said absorbent pad, and means whereby said pad and backing sheet may be detachably held together.

In testimony whereof I affix my signature.

MARTHA V. BAUER.